United States Patent
Denby, Jr.

(10) Patent No.: US 9,078,936 B1
(45) Date of Patent: Jul. 14, 2015

(54) CONTINUOUS ANTI-BACTERIAL DELIVERY APPARATUS AND METHOD

(71) Applicant: Donald J. Denby, Jr., Gulf Breeze, FL (US)

(72) Inventor: Donald J. Denby, Jr., Gulf Breeze, FL (US)

(*) Notice: Subject to any disclaimer, the term of this patent is extended or adjusted under 35 U.S.C. 154(b) by 37 days.

(21) Appl. No.: 13/815,576

(22) Filed: Mar. 11, 2013

(51) Int. Cl.
*A61L 2/00* (2006.01)
*G01N 21/00* (2006.01)
*G01N 23/00* (2006.01)
*A61L 2/10* (2006.01)

(52) U.S. Cl.
CPC ......................................... *A61L 2/10* (2013.01)

(58) Field of Classification Search
CPC ................ A61L 2/00; A61L 9/18; A61L 9/20
USPC .......... 422/22, 24; 250/454.11, 455.11, 492.1
See application file for complete search history.

(56) References Cited

U.S. PATENT DOCUMENTS

| 2009/0191100 A1 | 7/2009 | Deal |
| 2010/0140499 A1* | 6/2010 | Casale ............... 250/454.11 |
| 2010/0247374 A1* | 9/2010 | Pellet ..................... 422/24 |

\* cited by examiner

*Primary Examiner* — Monzer R Chorbaji
(74) *Attorney, Agent, or Firm* — J. Nevin Shaffer, Jr.

(57) ABSTRACT

A continuous anti-bacterial delivery apparatus and method consists of a fixture with an outside surface and an inside. An anti-bacterial delivery device is connected with the inside of the fixture and the anti-bacterial delivery device continuously delivers an anti-bacterial medium through the fixture to the outside surface of the fixture. A power source is connected with the anti-bacterial delivery device.

20 Claims, 1 Drawing Sheet

CONTINUOUS ANTI-BACTERIAL DELIVERY APPARATUS AND METHOD

CROSS REFERENCE TO RELATED APPLICATION

This application claims the benefit of previously filed U.S. provisional patent application No. 61/659,074 filed Jun. 13, 2012 for an "Ultraviolet Anti-Bacterial Delivery Device". The Applicant hereby claims the benefit of this provisional application under 35 U.S.C. §119. The entire content of this provisional application is incorporated herein by this reference.

FIELD OF THE INVENTION

This invention relates to a continuous anti-bacterial delivery apparatus and method. In particular, in accordance with one embodiment, the invention relates to a continuous anti-bacterial delivery apparatus consisting of a fixture with an outside surface and an inside. An anti-bacterial delivery device is connected with the inside of the fixture and the anti-bacterial delivery device continuously delivers an anti-bacterial medium through the fixture to the outside surface of the fixture. A power source is connected with the anti-bacterial delivery device.

BACKGROUND OF THE INVENTION

A problem exists with regard to the use of fixtures such as water faucets, door handles and toilet seats, for example only and not by way of limitation. The problem, simply put, is germs. Private and public buildings, offices, restaurants, hospitals, and the like, are accessed primarily by door handles. Inside, there are other fixtures a person encounters that must be touched to be used, such as water handles, toilet seats and the like. These useful fixtures are repositories of harmful germs. The need to eliminate contact with germs has led to the development of touchless water faucets and hand towel dispensers and the like. Nonetheless the vast majority of doors and sinks must be touched to be used and there is no viable "touchless" toilet seat so far as Applicant is aware.

Applicant is aware of the use of Ultra Violet (UV) light intermittently shown on the outside surface of fixtures as described in Deal, US Patent publication 2009/0191100. A major problem with such surface devices is they are not focused on a particular germ collecting surface as are individual devices and they are only operated intermittently.

Applicant is also aware of a device by Casale, US Patent publication 2010/0140499, that is a "self powered" sanitizing device located within a handle that produces UV light upon mechanical operation of the handle. While an improvement over Deal like devices because it is located within the fixture itself and thus directs the UV light at the most contaminated area of a fixture, Casale only operates intermittently. Such intermittent operation can not ensure the eradication of germs on the surface of the fixture. Further, Casale is clearly not functional for any non-movable fixture. That is, Casale requires the fixture to be moved to generate the UV light.

A further problem with prior art devices is that the protected surfaces are not identified such that a user can contact the protected surface in the dark, for example.

All terms used herein are given their common and customary meaning. Thus "anti-bacterial medium" describes a substance that kills bacteria such as UV light. It is well known that UV light and particularly UVC light is light of a wave length that has an anti-bacterial effect. That is, it kills germs. Any such "anti-bacterial medium" now known or hereafter developed is suitable for the purpose of the invention. Likewise, the term "continuously" identifies an uninterrupted constant, something that is always "on". As used herein, Applicant's device continuously directs the anti-bacterial medium from within the fixture to the surface of the fixture. Applicant has determined that the prior art intermittent devices simply do not operate long enough to ensure a germ free surface. "Power source" includes AC and DC outlets connected to power grids and/or batteries used as the power source or as a battery back up or any suitable continuous source of power now known or hereafter developed. "Through the fixture" describes the requirement that the anti-bacterial medium passes from the inside or bottom of the fixture to the outside of the fixture. The anti-bacterial medium may be located on the bottom of the fixture or within the fixture itself so long as it passes through the fixture to the outside surface of the fixture.

According to another aspect of the invention, the anti-bacterial medium is UV light. In another aspect, the anti-bacterial delivery device is connected with a Light Emitting Diode (LED) such that the UV light is directed to the surface of the fixture through the LED. In one aspect, the anti-bacterial delivery device also produces visible light and the visible light is directed to the surface of the fixture through the LED.

In another aspect, the power source is a continuous power source and in one aspect the power source is a battery power source.

In other aspects, the fixture is translucent, the fixture is a toilet seat or the fixture is a handle.

According to another embodiment of the invention, a continuous anti-bacterial delivery apparatus consists of a fixture with an outside surface and an inside. An anti-bacterial delivery device is connected with the inside of the fixture where the anti-bacterial delivery device continuously delivers an anti-bacterial medium through the fixture to the outside surface of the fixture. The anti-bacterial medium is UV light and the anti-bacterial delivery device is connected with an LED such that the UV light is directed to the surface of the fixture through the LED. And a continuous power source is connected with the anti-bacterial delivery device.

In one aspect, the anti-bacterial delivery device produces visible light and the visible light is directed to the surface of the fixture through the LED. In one aspect, the LED is located within the fixture on the inside of the fixture. In one aspect, the invention includes a battery back up power source and a low power indicator.

In further aspects, the fixture is translucent, the fixture is a toilet seat or the fixture is a handle.

According to another embodiment of the invention, a continuous anti-bacterial delivery method consists of:

a. providing a fixture with an outside surface and an inside; an anti-bacterial delivery device connected with the inside of the fixture where the anti-bacterial delivery device continuously delivers an anti-bacterial medium through the fixture to the outside surface of the fixture; and a power source connected with the anti-bacterial delivery device; and b. activating the power source.

In one aspect, the anti-bacterial medium is UV light. In another aspect, the anti-bacterial delivery device is connected with an LED such that UV light is directed to the surface of the fixture through the LED.

In another aspect, the power source is selected from a group consisting of: a continuous power source with a battery back up power source and a battery power source with a low power indicator.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
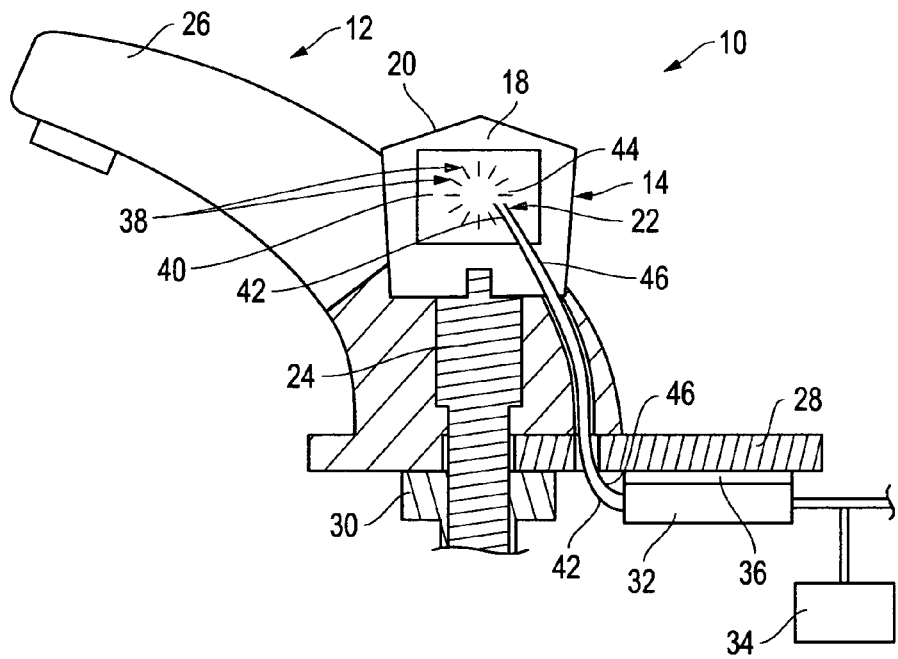
FIG. 1 is a partial cut away side view of the continuous anti-bacterial delivery apparatus of the present invention shown in a faucet handle.
Figure 2:
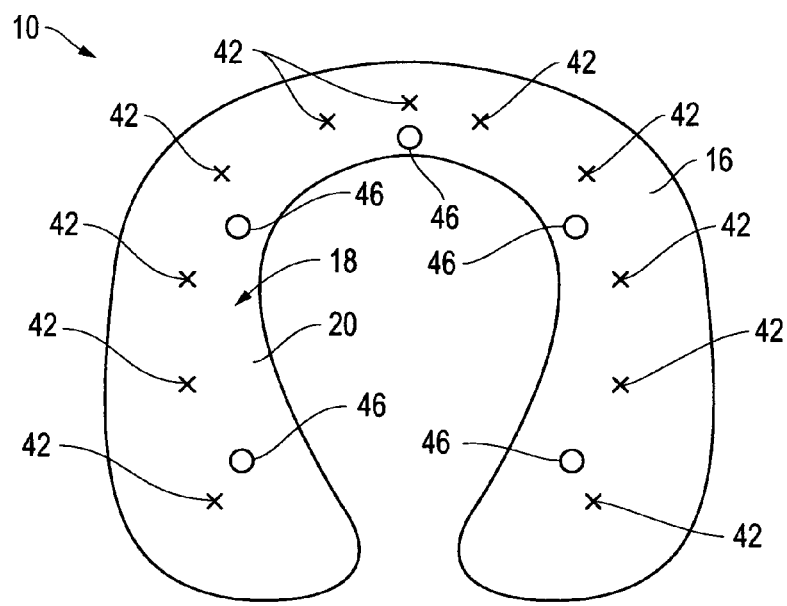
FIG. 2 is a top view of the invention of FIG. 1 in a toilet seat.

The preferred embodiment of the present invention is illustrated by way of example in FIGS. 1-2. With specific reference to FIG. 1, the continuous anti-bacterial delivery apparatus 10 according to a preferred embodiment includes a fixture 12. Again, as used herein fixture 12 may be a faucet handle 14 as illustrated or a toilet seat 16 as shown in FIG. 2 or any other similar such items upon which germs collect, by way of example only and not by limitation.

Fixture 12 has an inside 18 and an outside surface 20. FIG. 1 shows faucet handle 14 with a hollow space 22 on the inside 18. It may be that no such hollow space 22 is required as will be discussed more fully with regard to FIG. 2. Preferably, fixture 12 is at least translucent if not clear. Any material, such as glass or plastic, for example only, that is at least translucent is suitable.

Faucet handle 14 is shown connected to water valve 24 which is part of water faucet 26 connected to counter 28 by nut 30, all as known in the art and not disclosed more fully hereafter. Anti-bacterial delivery device 32 is connected with continuous power source 34 preferably a power station on the grid (not shown) as are known. Anti-bacterial delivery device 32 is any device that generates a germ killing medium, such as light having a wave length conducive to killing germs, such as UV light for example only. In one embodiment anti-bacterial delivery device 32 is connected with battery(ies) 36. Battery 36 may be the only source of continuous power or it may be used as a battery backup to power source 34 should power source 34 fail.

In one embodiment, anti-bacterial delivery device 32 produces an anti-bacterial medium 38 to the inside 18 of faucet handle 14. Preferably, again, the anti-bacterial medium 38 produced is UV light 40 transmitted by LED(s) 42 to the inside 18 and then through it to the outside surface 20 of fixture 12. Applicant has determined that it is not absolutely required that the elements of the invention, such as LED 42, be located inside fixture 12 as shown in FIG. 1. It is enough that the anti-bacterial medium 38 passes through the fixture to the outside surface 20. As LED(s) 42 are not subject to failure as are bulbs and lamps and as LED(s) 42 may be inserted in out of the way hard to reach places such as on or near toilet seat 16, Applicant prefers them as the delivery vehicle for the anti-bacterial medium 38.

In a preferred embodiment, anti-bacterial delivery device 32 produces visible light 44 that is delivered to the inside 18 of fixture 12 by LED 42 or by a separate LED 46 as shown. In this way, the outside surface 20 that is bathed in anti-bacterial medium 38 from the inside 18 of fixture 12 and is also illuminated. This feature, Applicant has found, is useful in indicating the protected area of the fixture 12 and as a night time safety light.

According to one aspect, where battery 36 is a primary continuous source of power or as a back up, anti-bacterial delivery device 32 monitors the battery life of battery 36 and creates a low power signal, such as a flashing LED 42 or any other suitable indicator. In this manner, a user is alerted to the need to replace battery 36 so that the fixture 12 is continuously bathed in anti-bacterial medium 38.

Referring now to FIG. 2, here the fixture 12 is a toilet seat 16. The important advantages of Applicant's invention are easily understood in this embodiment. Toilet seats 16 are not required to be moved in order to use them so it is important that Applicant's device functions perfectly in situations where the fixture is not moved. FIG. 2, shows LED 42 in the form of "X"s and LED 46 in the form of "O"s. LEDs 42 may located on the inside 18 translucent (or clear) toilet seat 16 and direct anti-bacterial medium 32, UV light, to the outside surface 20, as described above with reference to faucet handle 14. In one aspect of the invention, however, it is enough that the anti-bacterial medium 38 be directed to the underside of toilet seat 16 such that it passes through toilet seat 16 to the outside surface 20 and it is not required that the elements of the invention be placed within the fixture 12 itself. Importantly, Applicant's device continuously delivers anti-bacterial medium 38 thus ensuring the outside surface 20 is sanitary from use to use.

FIG. 2 also illustrates the advantage of LEDs 42 and/or LEDs 46 in providing an additional illumination to direct the user in low visibility situations. Additionally, as set forth above, low battery indicator in the form of flashing LED 42 and/or LED 46 ensures that the continuous anti-bacterial delivery apparatus 10 does not cease to function because the battery 36 was completely depleted.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A continuous anti-bacterial delivery apparatus comprising:
   a. a fixture with an outside surface and an inside;
   b. an anti-bacterial delivery device connected with said fixture wherein said anti-bacterial delivery device continuously delivers an anti-bacterial medium through said fixture to said outside surface of said fixture such that the entire fixture and the outside surface of the fixture receives said anti-bacterial medium; and
   c. a power source connected with said anti-bacterial delivery device wherein said power source is a continuous power source such that said anti-bacterial delivery device continuously delivers the anti-bacterial medium through said entire fixture to said outside surface.

2. The apparatus of claim 1 wherein said anti-bacterial medium is UV light.

3. The apparatus of claim 2 wherein said anti-bacterial delivery device is connected with an LED such that said UV light is directed to said surface of said fixture through said LED.

4. The apparatus of claim 3 wherein said anti-bacterial delivery device produces visible light and said visible light is directed to said surface of said fixture through said LED.

5. The apparatus of claim 1 wherein said power source is a battery power source.

6. The apparatus of claim 1 wherein said fixture is translucent.

7. The apparatus of claim 1 wherein said fixture is a toilet seat.

8. The apparatus of claim 1 wherein said fixture is a handle.

9. A continuous anti-bacterial delivery apparatus comprising:
   a. a fixture with an outside surface and an inside;
   b. an anti-bacterial delivery device connected with said fixture wherein said anti-bacterial delivery device continuously delivers an anti-bacterial medium through said fixture to said outside surface of said fixture wherein said anti-bacterial medium is UV light and wherein said anti-bacterial delivery device is connected with an LED such that said UV light is directed through said fixture to said surface of said fixture through said LED such that the entire fixture and the outside surface of the fixture receives said anti-bacterial medium; and
   c. a continuous power source connected with said anti-bacterial delivery device such that said anti-bacterial delivery device continuously delivers the anti-bacterial medium through said entire fixture and to said outside surface.

10. The apparatus of claim 9 wherein said anti-bacterial delivery device produces visible light and said visible light is directed to said surface of said fixture through said LED.

11. The apparatus of claim 9 wherein at least some of said LED is located on the inside of said fixture.

12. The apparatus of claim 11 further including a battery back-up power source and a low power indicator.

13. The apparatus of claim 9 wherein said fixture is translucent.

14. The apparatus of claim 9 wherein said fixture is a toilet seat.

15. The apparatus of claim 9 wherein said fixture is a handle.

16. A continuous anti-bacterial delivery method comprising:
   a. providing a fixture with an outside surface and an inside; an anti-bacterial delivery device connected with said fixture wherein said anti-bacterial delivery device continuously delivers an anti-bacterial medium through said fixture to said outside surface of said fixture such that the entire fixture and the outside surface of the fixture receives said anti-bacterial medium; and a power source connected with said anti-bacterial delivery device wherein said power source is a continuous power source such that said anti-bacterial delivery device continuously delivers the anti-bacterial medium through said entire fixture and to said outside surface; and
   b. activating said power source.

17. The method of claim 16 wherein said anti-bacterial medium is UV light.

18. The method of claim 17 wherein said anti-bacterial delivery device is connected with an LED such that UV light is directed to said surface of said fixture through said LED.

19. The method of claim 16 wherein said power source is selected from a group consisting of: a continuous power source with a battery hack up power source and a battery power source with a low power indicator.

20. The method of claim 16 further including a battery back up power source and a low power indicator.

* * * * *

UNITED STATES PATENT AND TRADEMARK OFFICE
CERTIFICATE OF CORRECTION

| | | |
|---|---|---|
| PATENT NO. | : 9,078,936 B1 | Page 1 of 1 |
| APPLICATION NO. | : 13/815576 | |
| DATED | : July 14, 2015 | |
| INVENTOR(S) | : Denby, Jr. | |

It is certified that error appears in the above-identified patent and that said Letters Patent is hereby corrected as shown below:

In the claims

Column 6, Line 26 claim 19: "battery hack up power source" should read --battery back up power source--.

Signed and Sealed this
Eighth Day of December, 2015

Michelle K. Lee
*Director of the United States Patent and Trademark Office*